(12) United States Patent
Lowe et al.

(10) Patent No.: US 7,550,637 B2
(45) Date of Patent: *Jun. 23, 2009

(54) CATALYST AND PROCESS FOR SELECTIVE HYDROGENATION

(75) Inventors: David M. Lowe, Sunnyvale, CA (US); Michel Molinier, Houston, TX (US); John D. Y. Ou, Houston, TX (US); Michael A. Risch, Seabrook, TX (US); Anthony F. Volpe, Jr., Santa Clara, CA (US); Jeffrey C. Yoder, San Jose, CA (US)

(73) Assignee: ExxonMobil Chemical Patents Inc., Houston, TX (US)

(*) Notice: Subject to any disclaimer, the term of this patent is extended or adjusted under 35 U.S.C. 154(b) by 782 days.

This patent is subject to a terminal disclaimer.

(21) Appl. No.: 11/203,862

(22) Filed: Aug. 15, 2005

(65) Prior Publication Data

US 2005/0288538 A1    Dec. 29, 2005

Related U.S. Application Data

(62) Division of application No. 10/720,558, filed on Nov. 24, 2003, now abandoned.

(51) Int. Cl.
*C07C 7/167* (2006.01)
(52) U.S. Cl. ............. 585/261; 585/262; 585/259
(58) Field of Classification Search .......... 585/259, 585/261, 262

See application file for complete search history.

(56) References Cited

U.S. PATENT DOCUMENTS

| | | | |
|---|---|---|---|
| 3,651,167 A | 3/1972 | Rosset |
| 3,793,232 A | 2/1974 | Duhaut et al. |
| 3,859,377 A | 1/1975 | Gross et al. |
| 4,149,961 A | 4/1979 | Antos |
| 4,207,169 A | 6/1980 | Courty et al. |
| 4,243,516 A | 1/1981 | Martino et al. |
| 4,401,557 A | 8/1983 | Juguin et al. |
| 4,420,420 A | 12/1983 | Mita et al. |
| 4,487,848 A | 12/1984 | Robinson et al. |
| 4,522,935 A | 6/1985 | Robinson et al. |
| 4,677,094 A | 6/1987 | Moser et al. |
| 4,691,070 A | 9/1987 | Nakamura et al. |
| 5,233,118 A | 8/1993 | Bricker et al. |
| 5,356,851 A | 10/1994 | Sarrazin et al. |
| 5,364,998 A | 11/1994 | Sarrazin et al. |
| 5,536,695 A | 7/1996 | Blejean et al. |
| 5,877,363 A | 3/1999 | Gildert et al. |
| 5,965,481 A | 10/1999 | Durand et al. |
| 6,084,140 A | 7/2000 | Kitamura et al. |
| 6,096,933 A | 8/2000 | Cheung et al. |
| 6,153,090 A | 11/2000 | Le Peltier et al. |
| 6,187,985 B1 | 2/2001 | Le Peltier et al. |
| 6,255,548 B1 | 7/2001 | Didillon et al. |
| 6,355,854 B1 | 3/2002 | Liu |
| 6,436,871 B1 | 8/2002 | Liu |
| 6,498,280 B1 | 12/2002 | Uzio et al. |
| 6,503,866 B1 | 1/2003 | Shepherd et al. |
| 6,514,904 B1 | 2/2003 | Moser et al. |
| 6,586,647 B1 | 7/2003 | Abrevaya et al. |
| 6,777,371 B2 | 8/2004 | Liu |
| 2002/0068843 A1 | 6/2002 | Dai et al. |
| 2002/0136686 A1 | 9/2002 | Takahashi |
| 2005/0113251 A1 | 5/2005 | Lowe et al. |
| 2005/0113613 A1 | 5/2005 | Molinier et al. |
| 2005/0113615 A1 | 5/2005 | Lowe et al. |

FOREIGN PATENT DOCUMENTS

| | | |
|---|---|---|
| WO | WO 98/47617 | 10/1998 |
| WO | WO 98/47618 | 10/1998 |
| WO | WO 98/47620 | 10/1998 |
| WO | WO 2004/046076 | 3/2004 |

OTHER PUBLICATIONS

Li, et al., "*Selective Catalytic Reduction of NO Over Metal Oxide or Noble Metal-Doped $In_2O_3/Al_2O_3$ Catalysts By Propene in the Presence of Oxygen*", Reaction Kinetics and Catalysis Letters, 2003, vol. 80, No. 1, pp. 75-80, XP008030692.

H. Scott Fogler, *Elements of Chemical Reaction Engineering*, 2nd Edition, PTR Prentice Hall, Inc., pp. 29-52 (1992).

J. M. Smith, *Chemical Engineering Kinetics*, McGraw-Hill Book Company, pp. 231-279 (1956).

S. Asplund, "*Coke Formation and Its Effect on Internal Mass Transfer and Selectivity in Pd-Catalysed Acetylene Hydrogenation*", Journal of Catalysis, vol. 158, pp. 267-278 (1996).

*Primary Examiner*—Thuan Dinh Dang

(57) ABSTRACT

A selective hydrogenation catalyst composition comprises at least two different metal components selected from Groups 8 to 10 of the Periodic Table of Elements, one of which may be rhodium, and at least one metal component selected from Group 13 of the Periodic Table of Elements, such as indium.

18 Claims, No Drawings

CATALYST AND PROCESS FOR SELECTIVE HYDROGENATION

CROSS REFERENCE TO RELATED APPLICATIONS

The present application is a divisional application of U.S. patent application Ser. No. 10/720,558 filed Nov. 24, 2003 now abandoned and is related by subject matter to U.S. patent application Ser. No. 10/720,617 filed Nov. 24, 2003 and U.S. patent applications Ser No. 10/720,607 filed Nov. 24, 2003 filed concurrently herewith, the entire contents of which applications are incorporated herein by reference.

FIELD

This invention relates to a catalyst and a process for the selective hydrogenation of alkynes and diolefins to olefins.

BACKGROUND

Light olefins, such as ethylene, propylene and butylenes, can be produced using various processes such as steam cracking, fluid catalytic cracking, conversion of methanol to olefins, paraffin dehydrogenation, alcohol dehydration, methane coupling and Fischer Tropsch reactions. However, these processes often produce varying levels of acetylenic or diene by-products, such as acetylene, methyl acetylene (MA), propadiene (PD), butyne and butadiene. These by-products must be removed from the light olefin streams because they can act as poisons to the downstream processing catalysts, such as polymerization catalysts. The preferred method of removing these by-products is by selective hydrogenation in which, for example, the acetylenes are converted to ethylene, methyl acetylene and propadiene are converted to propylene, and the butyne and butadiene are converted to butylenes.

Currently, the commercial catalysts used for this selective hydrogenation comprise nickel or palladium, such as palladium and silver, on an alumina support. However, in addition to producing the desired olefin products, these catalysts tend to generate significant quantities of saturates (for example, ethane, propane and butanes) as a result of over-hydrogenation and green oil (olefin legumes) as a result of competing oligomerization reactions. Both of these by-products are undesirable in that they reduce the selectivity to the required light olefins. However, the green oil is particularly problematic in that it decreases the life of the hydrogenation catalyst.

There is therefore a need for an improved catalyst for the selective hydrogenation of alkynes and diolefins, wherein the catalyst exhibits increased olefin selectivity and reduced selectivity to saturates and oligomers, such as green oil, while retaining high hydrogenation activity.

U.S. Patent Application Publication No. 2002/0068843 discloses a catalyst for selectively hydrogenating acetylenic and diolefinic compounds with low green oil formation, the catalyst comprising the following active components loaded on a porous inorganic support: (1) at least one of platinum, palladium, nickel, ruthenium, cobalt, and rhodium; (2) at least one of silver, copper, zinc, potassium, sodium, magnesium, calcium, beryllium, tin, lead, strontium, barium, radium, iron, manganese, zirconium, molybdenum, and germanium; (3) at least one rare earth metal selected from scandium, yttrium, and Lanthanides in Group IIIB of Periodic Table of Elements; and (4) bismuth. Preferably, component (1) is platinum or palladium; component (2) is silver, potassium, or sodium; and component (3) is lanthanum or neodymium.

U.S. Pat. No. 6,355,854 discloses a method for the oxidative dehydrogenation of an alkane having from 2 to 4 carbon atoms comprising contacting said alkane in the presence of oxygen to a material having the empirical formula

$$Ni_xA_jB_kC_lO_i$$

wherein Ni is nickel and x is in the range of about 0.05-0.96; A is a metal selected from the group consisting of cobalt, niobium, tantalum and combinations thereof and j is in the range of from about 0.05-0.8; B is a dopant selected from the group consisting of lithium, sodium, potassium, rubidium, cesium, magnesium, calcium, strontium, barium, manganese, lanthanum, cerium, praseodymium, neodymium, samarium and combinations thereof and k is in the range of from 0-0.5; C is a dopant selected from the group consisting of tin, aluminum, iron, silicon, boron, antimony, titanium, indium, germanium, chromium, lead and combinations thereof and l is in the range of from 0-0.5; i is a number that satisfies the valence requirements of the other elements present; and the sum of j, k and l is at least 0.15.

U.S. Pat. No. 6,255,548 discloses a method for selectively hydrogenating a feed comprising an acetylenic compound and/or a diolefin in the presence of a catalyst comprising at least one support, at least one Group VIII metal selected from nickel, palladium, platinum, rhodium, ruthenium and iridium and at least one additional element M selected from germanium, tin, lead, rhenium, gallium, indium, thallium, gold, and silver, wherein the catalyst is formed by introducing said additional element M into an aqueous solvent in the form of at least one water-soluble organometallic compound comprising at least one carbon-M bond. The preferred Group VIII metals are nickel, palladium and platinum and the preferred additional elements M are germanium, tin, gold, and silver.

U.S. Pat. No. 5,877,363 discloses a process for the removal of acetylenes and 1,2-butadiene from a $C_4$ aliphatic hydrocarbon stream by contacting the hydrocarbon stream with hydrogen in a distillation column reactor containing a bed of hydrogenation catalyst comprising a Group VIII metal selected from platinum, palladium, rhodium or mixtures thereof; optionally in combination with a Group IB or Group VIB metal, and fractionally distilling the reaction mixture to remove a heavier fraction and removing a fraction overhead comprising substantially all of the $C_4$ compounds having reduced acetylenes and 1,2-butadiene content. The preferred hydrogenation catalyst is palladium.

U.S. Pat. Nos. 5,356,851 and 5,364,998 disclose a catalyst and a process for the selective hydrogenation of unsaturated compounds, wherein the catalyst contains 0.1 to 10% of at least one Group VIII metal selected from nickel, palladium, platinum, rhodium and ruthenium and 0.01 to 10% of at least one Group IIIA metal selected from gallium and indium. The molar ratio of Group IIIA metal to Group VIII metal is between 0.2 and 5, preferably between 0.3 and 2. The metals are deposited on a catalyst support by (a) impregnating the support with a solution of a Group IIIA metal compound precursor, then (b) impregnating the product of (a) with a solution of a Group VIII metal compound and then (c) calcining the product of (b) at 110 to 600° C. The preferred Group VIII metals are nickel, palladium and platinum.

In U.S. Pat. No. 4,691,070 a catalyst for the hydrogenation of a diolefin is disclosed in which palladium or a compound thereof and at least one co-catalyst component selected from ruthenium, rhodium, cobalt, and rhenium are supported each in the form of an elemental metal or a metal compound on a non-acidic support.

A rhodium catalyst is disclosed in U.S. Pat. No. 4,420,420 in which active rhodium metal is supported on a silica type or titania type support, optionally together with one or more co-catalysts including alkaline earth metals, such as calcium, magnesium, barium and the like, noble metals, such as platinum, palladium, iridium, ruthenium, gold and the like, iron, nickel, cobalt, cerium and manganese.

Co-pending U.S. patent application Ser. No. 10/720,617, filed Nov. 24, 2003, filed concurrently herewith, describes a catalyst and process for selectively hydrogenating alkynes and/or diolefins, wherein the catalyst comprises (a) a rhodium component present in an amount such that the catalyst composition comprises less than 3.0% of rhodium by weight of the total catalyst composition; and (b) an indium component present in an amount such that the catalyst composition comprises at least 0.4% and less than 5.0% of indium by weight of the total catalyst composition.

SUMMARY

In one aspect, the present invention resides in a catalyst composition comprising at least two metal components selected from Groups 8 to 10 of the Periodic Table of Elements and at least one metal component selected from Group 13 of the Periodic Table of Elements.

In one embodiment, one of said at least two metal components selected from Groups 8 to 10 of the Periodic Table of Elements is rhodium. Conveniently, another of said at least two metal components is selected from one or more of iron, ruthenium and cobalt.

Conveniently, said at least one metal component selected from Group 13 of the Periodic Table of Elements is indium.

In another aspect, the present invention resides in a catalyst composition comprising:
(a) a first component comprising rhodium;
(b) a second component comprising at least one metal selected from Group 13 of the Periodic Table of Elements; and
(c) a third component comprising at least one metal different from said first and second components and selected from Groups 1 to 15 of the Periodic Table of Elements.

Conveniently, said second component comprises indium.

In one embodiment, said third component comprises at least one metal selected from Groups 8 to 10 of the Periodic Table of Elements and in particular is selected from one or more of iron, ruthenium and cobalt.

In yet another aspect, the invention resides in a catalyst composition comprising:
(a) a first component comprising rhodium;
(b) a second component comprising indium; and
(c) a third component selected from one or more of iron, ruthenium and cobalt.

In a further aspect, the invention resides in a method of making a catalyst composition, the method comprising:
(a) applying a rhodium compound to a support;
(b) applying a compound of a metal selected from Group 13 of the Periodic Table of Elements to the support; and
(c) applying a compound of a further metal different from rhodium and from said Group 13 metal and selected from Groups 1 to 15 of the Periodic Table of Elements to the support.

Conveniently, said further metal compound is applied to the support before either the rhodium compound or the Group 13 metal compound.

Conveniently, the Group 13 metal compound is applied to the support either concurrently with or before the rhodium compound.

Conveniently, after (a), and/or (b) and/or (c), the support is calcined at a temperature of about 100° C. to about 600° C.

In yet a further aspect, the invention resides in use of any of the catalyst compositions described above or more particularly described hereinafter in a process for selectively removing alkynes and/or diolefins, particularly alkynes and/or diolefins having 2 to 4 carbon atoms, from a feedstock containing olefins, particularly $C_2$ to $C_4$ olefins.

DETAILED DESCRIPTION OF THE EMBODIMENTS

The present invention relates to a novel catalyst composition, its preparation and its use in the hydrogenation of alkynes and diolefins in a feedstock containing other unsaturated compounds, such as olefins. The catalyst composition comprises at least two different metals from Groups 8 to 10 of the Periodic Table of Elements, one of which is typically rhodium, and at least one metal selected from Groups 1 to 15, typically Group 13, of the Periodic Table of Elements, typically indium. The catalyst composition is capable of hydrogenating the alkynes and diolefins in the feedstock with high selectivity to olefins and low selectivity to green oil (oligomers) and saturates. An additional benefit of the present catalyst composition is the extension of catalyst lifetime and/or operating cycle due to the reduction in green oil formation.

The Periodic Table of Elements referred to herein is the IUPAC version described in the *CRC Handbook of Chemistry and Physics*, 78th Edition, CRC Press, Boca Raton, Fla. (1997).

As used herein, the term "acetylene" includes the hydrocarbon $C_2H_2$ as well as other acetylenic hydrocarbons, such as methyl acetylene (MA). The term "ethylene product stream" includes streams containing the hydrocarbon $C_2H_4$ as well as streams containing other mono- and diolefinically unsaturated hydrocarbons. It will be appreciated, however, that while the catalysts are often discussed in terms of selectively hydrogenating acetylene, MA, propadiene (PD) and optionally, butadiene (BD) in a stream that is predominantly ethylene, propylene and/or butylenes, they are not necessarily limited to the treatment of streams that contain ethylene or propylene or butene, but are expected to find applicability to the selective hydrogenation of other unsaturated compounds in streams of other chemical content as well.

Catalyst Composition

The present catalyst composition comprises three or more metals or metal-based components that may be combined with a binder and/or a support. The term "component" is used to include a metal compound that may not be purely the elemental metal.

In one embodiment, the catalyst composition includes:
(a) a first component which includes a metal selected from Groups 8 to 10 of the Periodic Table of Elements and normally comprises rhodium;
(b) a second component which includes a metal selected from Group 13 of the Periodic Table of Elements and which normally comprises indium; and
(c) a third component which also includes a metal selected from Groups 8 to 10 of the Periodic Table of Elements but which is different from the first component metal and normally comprises one or more of iron, cobalt and/or ruthenium.

In another embodiment, the catalyst composition includes:
(a) a first component comprising rhodium;

(d) a second component comprising at least one metal selected from Group 13 of the Periodic Table of Elements; and (e) a third component comprising at least one metal different from said first and second components and selected from Groups 1 to 15 of the Periodic Table of Elements.

The catalyst composition conveniently comprises from about 0.01 wt % to about 20 wt %, such as from about 0.04 wt % to about 5 wt %, of the first component. Where the first component is rhodium or a rhodium compound, the catalyst composition typically comprises from about 0.01 wt % to about 10 wt %, such as from about 0.04 wt % to about 5 wt %, of rhodium.

The catalyst composition conveniently comprises from about 0.01 wt % to about 30 wt %, such as from about 0.04 wt % to about 20 wt %, of the second component. Where the second component is indium or an indium compound, the catalyst composition typically comprises from about 0.01 wt % to about 20 wt %, such as from about 0.04 wt % to about 10 wt %, of indium.

The catalyst composition conveniently comprises from about 0.01 wt % to about 50 wt %, such as from about 0.05 wt % to about 30 wt %, of the third component. Where the third component is iron or an iron compound, the catalyst composition typically comprises from about 0.05 wt % to about 30 wt %, such as from about 0.1 wt % to about 20 wt %, of iron. Where the third component is cobalt or a cobalt compound, the catalyst composition typically comprises from about 0.05 wt % to about 30 wt %, such as from about 0.1 wt % to about 25 wt %, of cobalt. Where the third component is ruthenium or a ruthenium compound, the catalyst composition typically comprises from about 0.05 wt % to about 10 wt %, such as from about 0.1 wt % to about 5 wt %, of ruthenium.

All weight percentages for the metal components of the catalyst composition are based on the amount of elemental metal present by weight of the total catalyst composition, including any binder or support.

In general, the molar ratio of the first component metal to the second component metal is from about 0.1 to about 1.2, such as from about 0.3 to about 0.9, whereas the molar ratio of the first component metal to the third component metal is about 0.001 to about 0.6, such as about 0.002 to about 0.3.

In addition to the active metal components discussed above, the catalyst composition may also include a support or binder material. Suitable support materials comprise carbon, silicon nitride, silicon carbide, boron nitride, magnesium silicate, bentonite, zeolites, metal alloys, zirconia, alumina, silica, silica-alumina, ceria-alumina, aluminates (such as aluminates of Groups 1 and 2 of the Periodic Table of Elements), and magnesium oxide-silicon oxide mixtures. Preferred support materials include zirconia, alumina, and ceria-alumina. The binder or support material conveniently comprises from about 50 wt % to about 99.9 wt %, such as from about 65 wt % to about 99.5 wt %, of the entire catalyst composition.

In general, the first, second and third components are present in the catalyst composition in elemental form, but one or more of these components may also be present at least partly in other forms, such as oxide, hydride or sulfide forms.

Each of the active metal components may be substantially uniformly distributed throughout the support, can be located within a thin layer at the support surface (commonly referred to as eggshell), can be located at the center of the support (commonly referred to as eggyolk), or can be concentrated between the outer edge and the center of the support (commonly referred to as eggwhite). Preferably, the metal components are concentrated in a thin layer (not more than 1000 microns, conveniently not more than 500 microns, such as not more than 300 microns, for example not more than 100 microns deep) on the surface of the support.

Method of Making the Catalyst Composition

The catalyst composition can be prepared by a variety of different procedures. One suitable procedure is by impregnation in which a support, such as alumina, is contacted with an aqueous or organic solution of a compound (such as a nitrate, sulfate, halide, formate, acetate, citrate, oxoacetate, oxalate and acetylacetonate) of the chosen metal or metals, the solution volume being less than, equal to or in excess of the retention volume of the support. After maintaining contact between the support and the solution for about 0.01 to about 24 hours, such as about 0.05 to about 4 hours, the impregnated support is dried and normally calcined under air normally at between 100 and 650° C. and preferably between 110 and 600° C. Such a procedure can be used to apply a plurality of active components to the support in a single operation or alternatively separate impregnations can be used to apply the active components successively to the support.

Alternatively, the metal components can be applied to the support by mixing a slurry or solution of a compound of the chosen metal or metals with a slurry of a particulate support in a liquid, such as water. After mixing, the resultant slurry may be treated, such as by heating or vacuum drying, to partially or completely remove the liquid, whereafter the treated support may, if necessary, be filtered, then washed with distilled water, dried and calcined as in the case of the impregnation procedure.

As a further alternative, the metal components can be applied to the support by precipitation. For example, a liquid solution, such as an aqueous solution, comprising a source of ions of one of the active components can be subjected to conditions sufficient to cause precipitation of the component as a solid from solution, such as by the addition of a precipitating reagent to the solution. Conveniently, the precipitation is conducted at a pH above 7. For example, the precipitating agent may be a base such as sodium hydroxide or ammonium hydroxide.

In addition, two or more of the active metal components can be applied to the support simultaneously by co-precipitation. For example, a first liquid solution comprising a source of ions of one of the active components can be combined with a second liquid solution comprising a source of ions of another component. This combination of two solutions can take place under conditions sufficient to cause co-precipitation of both components onto the support from the liquid medium. Alternatively, the source of ions of the one component and the source of ions of the other component may be combined into a single solution. This solution may then be subjected to conditions sufficient to cause co-precipitation of the solid components onto the support, such as by the addition of a precipitating reagent to the solution.

Although any compound of the desired metal can be used to apply the different catalyst components to the support, it is found that in the case of rhodium, the preferred compound used to apply the rhodium to the support is rhodium nitrate. In the case of indium, the preferred compounds are indium nitrate and indium formate. In the case of iron, the preferred compounds are iron nitrate and iron ammonium oxalate. In the case of ruthenium, the preferred compound is ruthenium nitrosyl nitrate. In the case of cobalt, the preferred compounds are cobalt nitrate, acetate and formate.

In addition, although the different catalyst components can be applied to the support in any order and any combination, in one preferred embodiment, the third catalyst component is added to the support, such as by impregnation, prior to the addition of either or both of the first and second components. Thereafter, the first and second components can be simultaneously added to the support or the second component can be added to the support before the first component.

After applying the metal components to the support, the support is normally calcined, such as in air, at between about 100° C. and about 600° C., for example at between about 110° C. and about 500° C. Where the metal components are applied to the support in consecutive steps, a separate calcination step can be conducted after each metal application step or a single calcination step can be conducted after all the metal components have been applied to the support.

Finally, the catalyst composition is conveniently heated in a reducing atmosphere, such as an atmosphere containing about 5 to about 30 mol % hydrogen, with the remainder being an inert gas, such as nitrogen, at a temperature of about 100° C. to about 650° C., such as about 200° C. to about 500° C., to further increase the activity of the catalyst. Such a reduction step can be performed in addition to, or in place of, the calcination step(s) referred to above.

Selective Hydrogenation Process

The catalyst composition of the invention is capable of hydrogenating alkynes and/or diolefins in a feedstock that also contains olefins with high selectivity to olefins and low selectivity to green oil (oligomers formed from two or more alkyne and/or diolefin molecules) and saturates. In particular, when used to selectively hydrogenate $C_2$ to $C_4$ alkynes and/or diolefins in a feedstock also containing $C_2$ to $C_4$ olefins, the present catalyst composition typically achieves an alkyne conversion in excess of 80%, such as in excess of 90%, with an olefin selectivity in excess of 50%, such as in excess of 60%, and a green oil selectivity of less than 10%, such as less than 8%. The reduction in green oil formation should also result in an extension of catalyst lifetime and/or operating cycle.

The selective hydrogenation of acetylene, methyl acetylene (MA), propadiene (PD), and/or butadiene (BD) is typically carried out in one of four unit types:
  (a) Front-End Selective Catalytic Hydrogenation Reactors, where the feed is composed of $C_3$ and lighter hydrocarbons, or $C_2$ and lighter hydrocarbons. In the case of raw gas applications, other components such as butadiene, ethyl acetylene, dimethyl acetylene, vinyl acetylene, cyclopentadiene, benzene, and toluene can also be present.
  (b) Back-End Selective Catalytic Hydrogenation Reactors, where the feed is composed of an ethylene-rich stream.
  (c) MAPD Selective Catalytic Hydrogenation Reactors, where the feed is composed of a propylene-rich stream.
  (d) BD Selective Catalytic Hydrogenation Reactors, where the feed is composed of a butylene-rich stream.

The operating parameters of an alkyne/alkadiene selective hydrogenation process are not narrowly critical and can be controlled in view of a number of interrelated factors including, but not necessarily limited to, the chemical composition of the feedstock, the control systems and design of a particular plant, etc. (i.e., different reactor configurations including front-end, tail-end, MAPD, and BD converters as mentioned briefly above). In general, however, suitable operating parameters include a temperature of from about 20° C. to about 150° C., such as from about 30° C. to about 100° C., a pressure of from about 100 psig to about 580 psig (690 kPa to 4100 kPa), such as from about 200 psig to about 440 psig (1400 kPa to 3400 kPa), a $H_2/C_2H_2$ molar feed ratio of from about 1 to about 1000, such as of from about 1.1 to about 800 and, assuming the reaction is in the vapor phase, a GHSV from about 100 to about 20,000, such as from about 500 to about 15,000 or, if the reaction is in the liquid phase, an LHSV of 0.1 to 100, such as from 1 to 25.

The following descriptions serve to illustrate how the inventive process may be practiced in the different commercial units.

In the case of a front-end (FE) selective hydrogenation reactor, the inlet operating temperature may range from about 30 to about 150° C., such as from about 50 to about 100° C. Representative operating pressures may range from about 100 psig to about 500 psig (about 690 to 3,500 kPa), such as from about 200 psig to about 400 psig (about 1400 to 2800 kPa). The GHSV may range from about 5000 to about 20,000, such as from about 8000 to about 15,000. Further, the $H_2$ partial pressure may range from about 25 psig to about 175 psig (about 172 to 1200 kPa), such as from about 50 psig to about 140 psig (about 345 to 965 kPa). The feedstreams in FE selective hydrogenation processes typically contain at least about 20% ethylene, and less than 1% acetylene, with the balance comprising ethane, methane, hydrogen and small amounts of similarly light components. (All percentages are mole % unless otherwise noted). Depending upon the process configuration of the plant, this feed stream can also contain $C_3$ components such as methyl acetylene, propadiene, propylene, and propane. Still heavier components such as 1,3 butadiene; 1,2 butadiene; ethyl acetylene; dimethyl acetylene; vinyl acetylene; cyclopentadiene; benzene; toluene and mixtures thereof may also be present as a result of certain process configurations.

In the case of a back-end selective hydrogenation reactor, the inlet operating temperature may range from about 30 to about 150° C., such as from about 40 to about 90° C. Representative operating pressures may range from about 100 psig to about 500 psig (about 690 to 3500 kPa), such as from about 200 psig to about 400 psig (about 1400 to 2800 kPa). The GHSV may range from about 1000 to about 10,000, such as from about 3000 to about 8000. Further, the $H_2/C_2H_2$ molar feed ratio may range from about 0.5 to about 20, such as from about 1.0 to about 1.5. The feedstreams in back-end selective hydrogenation processes may contain about 2% acetylene, about 70% ethylene, and the balance other $C_2$ compounds.

In the case of a methyl acetylene/propadiene (MAPD) selective hydrogenation reactor, operation can be conducted in either the liquid or vapor phase. In the case of liquid phase operation, the inlet operating temperature may range from about 20 to about 100° C., such as from about 30 to about 80° C. Representative operating pressures may range from about 150 psig to about 600 psig (about 1000 to 4100 kPa), such as from about 250 psig to about 500 psig (about 1700 to 3400 kPa). The LHSV may range from about 0.1 to about 100, such as from about 1 to about 10. In the case of the vapor phase operation, the inlet operating temperature may range from about 20 to about 600° C., such as from about 200 to about 400° C. Representative operating pressures may range from about 150 psig to about 600 psig (about 1000 to 4100 kPa), such as from about 250 psig to about 500 psig (about 1700 to 3400 kPa). The GHSV may range from about 100 to about 20,000, such as from about 500 to about 5000. Further, the $H_2/C_2H_2$ molar feed ratio may range from about 0.5 to about 20, such as from about 1 to about 10. The feedstreams in MAPD selective hydrogenation processes may contain at least 80% propylene, and less than 10% of a compound selected from the group consisting of methyl acetylene, propadiene, and mixtures thereof.

In the case of a butadiene (BD) selective hydrogenation reactor, operation can be conducted in either the liquid or vapor phase. In the case of liquid phase operation, the inlet operating temperature may range from about 20 to about 120° C., such as from about 40 to about 100° C. Representative operating pressures may range from about 150 psig to about 600 psig (about 1000 to 4100 kPa), such as from about 200 psig to about 400 psig (about 1400 to 2800 kPa). The LHSV may range from about 0.1 to about 100, such as from about 1 to about 25. In the case of the vapor phase operation, the inlet operating temperature may range from about 20 to about 600° C., such as from about 50 to about 200° C. Representative operating pressures may range from about 150 psig to about 600 psig (about 1000 to 4100 kPa), such as from about 250 psig to about 500 psig (about 1700 to 3400 kPa). The GHSV may range from about 100 to about 20,000, such as from about 500 to about 5000. Further, the $H_2/C_2H_2$ molar feed ratio may range from about 0.5 to about 20, preferably from about 1 to about 10. The feedstreams in BD selective hydrogenation processes may contain at least 90% butylene, and greater than 0.2% butadiene.

The invention will now be more particularly described with reference to the following Examples.

In the Examples, the following definitions are employed:

$C_2H_2$ Conversion:

$$\frac{(C_2H_2)_{in} - (C_2H_2)_{out}}{(C_2H_2)_{in}} \times 100$$

$C_2H_4$ (Gain) Selectivity:

$$\frac{(C_2H_2)_{in} - (C_2H_2)_{out} - C_2H_{6\,produced} - (2 \times C_{4\,produced} + 3 \times C_{6\,produced})}{(C_2H_2)_{in} - (C_2H_2)_{out}} \times 100$$

$C_2H_6$ Selectivity:

$$\frac{C_2H_{6\,produced}}{(C_2H_2)_{in} - (C_2H_2)_{out}} \times 100$$

Green-Oil Selectivity:

$$\frac{(2 \times C_{4\,produced}) + (3 \times C_{6\,produced})}{(C_2H_2)_{in} - (C_2H_2)_{out}} \times 100$$

EXAMPLE 1 (COMPARATIVE)

Pd—Ag Catalyst

This example illustrates the performance of a current state of the art commercial Pd-based catalyst. The catalyst, G-58C, was obtained from Sud-Chemie, Inc. and comprised 0.03 wt % Pd and 0.18 wt % Ag on alumina. The catalyst was prereduced at 120° C. for 2 hours under a 100% hydrogen atmosphere and was then evaluated under the following conditions: temperature=100° C., pressure=300 psig, GHSV=4500, $H_2/C_2H_2$ feed ratio=1.1. The hydrocarbon feed contained nominally 1.65 mole % acetylene and 70 mole % ethylene, with balance being nitrogen. Impurities that may be present in the feed include carbon monoxide (<0.5 ppm), mercury, arsine, phosphorus (<5 ppb), sulfur (<1 ppm), oxygen (<1 ppm), water (<10 ppm), acetone (<10 ppm) and methanol (<2 ppm). Test results at 100% hydrogen conversion are given in Table 1 below.

TABLE 1

| Catalyst (wt %) | $C_2H_2$ conv (%) | $C_2H_4$ select (%) | Green Oil select (%) |
|---|---|---|---|
| 0.03% Pd/0.18% Ag | 84.8 | 60.1 | 24.6 |

It will be seen that the conventional catalyst had an ethylene selectivity of about 60% but its green oil selectivity was almost 25%.

EXAMPLE 2 (COMPARATIVE)

Rh—In Bimetallic Catalyst

A rhodium/indium bimetallic catalyst of the type described in our co-pending U.S. patent application Ser. No. 10/720,617 filed Nov. 24, 2003, filed concurrently herewith, was prepared and tested as follows.

10 g of theta-alumina (SBa-90 supplied by Sasol) were mixed with 50 ml of deionized water to form a slurry. Then 0.189 gm $Rh(NO_3)_3 \cdot 2H_2O$ was dissolved in 80 ml deionized water and was mixed with 0.314 g $In(NO_3)_3 \cdot xH_2O$ dissolved in 50 ml deionized water. The solution containing both metals was added to the alumina slurry and, after 1 hour stirring, the slurry was gently heated until most of the water was removed. The resulting paste was dried in a vacuum oven for 2 hours at 100° C., whereafter the remaining powder was calcined in air for 2 hours at 120° C. and then for 4 hours at 450° C. The resultant catalyst composition was then reduced at 350° C. for 5 hours in a nitrogen atmosphere containing 5 mol % hydrogen.

The final catalyst contained 0.6 wt % rhodium and 1.2 wt % indium and had a rhodium to indium molar ratio of 0.5. When the catalyst was used to treat the same hydrocarbon feed under the same conditions as Example 1, the results shown in Table 2 were obtained. Table 2 also gives the results obtained with the catalyst of Example 1 (but with the prereduction regime of Example 2) after the same time on stream (TOS).

TABLE 2

| Catalyst (wt %) | TOS (hrs) | $C_2H_2$ conv (%) | $C_2H_4$ select (%) | $C_2H_6$ select (%) | Green Oil select (%) |
|---|---|---|---|---|---|
| 0.6% Rh/1.2% In | 11 | 80.5 | 40.6 | 51.7 | 7.7 |
| 0.03% Pd/0.18% Ag | 11 | 93.2 | 50.8 | 24.8 | 24.5 |

It will be seen that the green oil selectivity of the Example 2 catalyst was less than one third of that of the catalyst of Example 1.

EXAMPLE 3

Rh—In-Metal Trimetallic Catalysts

A series of trimetallic catalysts were prepared each containing 0.6 wt % rhodium, 1.2 wt % indium and 0.6 wt % of a third metal selected from Groups 2 to 15 of the Periodic Table of Elements on an alumina support. In each case, the alumina support was Norton SA6175 alumina which had been heat treated at 975° C. for 15 minutes to convert the gamma phase alumina to the theta phase.

Each catalyst was prepared as follows. Rhodium nitrate (10.01 wt % solution) obtained from Strem Chemicals was diluted to 2.50 wt % rhodium with deionized water. Solid indium nitrate trihydrate obtained from Prochem was dissolved to 6.56 wt % indium using deionized water. 169.1 μL of the diluted rhodium nitrate solution and 117.7 μL of the prepared indium nitrate solution were mixed with deionized water (313.1 μL). This mixed rhodium-indium solution (120 μL) was added to 148 mg of alumina in a vial and agitated by vibration for 30 minutes at room temperature. The obtained material was dried at 120° C. for 3 hours and then calcined in air at 450° C. for 4 hours to afford a sample containing 0.6 wt % rhodium and 1.2 wt % indium supported on theta alumina. Separately prepared calcined samples were then used as the starting materials for the second impregnation steps for each catalyst as described below.

0.6% Scandium: Scandium nitrate solution was prepared by dissolving solid scandium nitrate hydrate as obtained from Aldrich to 4.53 wt % metal using deionized water. The prepared scandium nitrate solution (189.7 μL) was mixed with deionized water (1250.3 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Yttrium: Yttrium nitrate solution was prepared by dissolving solid yttrium nitrate hydrate as obtained from Aldrich to 9.63 wt % metal using deionized water. The prepared yttrium nitrate solution (85.8 μL) was mixed with deionized water (1354.2 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Lanthanum: Lanthanum nitrate solution was prepared by dissolving solid lanthanum nitrate hydrate as obtained from Aldrich to 12.68 wt % metal using deionized water. The prepared lanthanum nitrate solution (64.2 μL) was mixed with deionized water (1375.8 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Titanium: Ammonium titanyl oxalate solution was prepared by dissolving solid ammonium titanyl oxalate hydrate as obtained from Aldrich to 4.61 wt % metal in deionized water. The prepared ammonium titanyl oxalate solution (195.9 μL) was mixed with deionized water (1244.1 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% zirconium: Zirconyl nitrate solution was prepared by diluting the zirconyl nitrate solution as obtained from Aldrich as a solution in dilute nitric acid to 14.6 wt % metal using deionized water. The prepared zirconyl nitrate solution (50.3 μL) was mixed with deionized water (1389.7 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Hafnium: Hafnium acetylacetonate solution was prepared by mixing solid hafnium acetylacetonate as obtained from Strem Chemicals with deionized water and nitric acid. The mixture was heated to 60° C. until homogeneous. The final concentrations were 7.57 wt % hafnium and 5.3 wt % nitric acid. The prepared hafnium acetylacetonate solution (129.1 μL) was mixed with deionized water (1310.9 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Vanadium: Solid vanadium pentoxide as obtained from Aldrich was mixed with 1 M solution of oxalic acid in deionized water and the resultant mixture was diluted with deionized water to the desired concentration. The mixture was heated until a deep blue color was achieved and the solution became homogeneous. The resultant vanadium oxalate solution (6.88 wt % vanadium, 131.3 μL) was mixed with deionized water (1308.7 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Niobium: Niobium oxalate solution was prepared by dissolving solid ammonium niobium oxalate as obtained from Aldrich to 4.647 wt % metal in deionized water. The prepared niobium oxalate solution (202.9 μL) was mixed with deionized water (1237.1 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Tantalum: Tantalum (V) ethoxide as obtained from Aldrich was mixed with a 1 M solution of oxalic acid in deionized water and the resultant mixture was heated at 60° C. until homogeneous. The resultant tantalum oxalate solution (9.0 wt % tantalum, 102.1 μL) was mixed with deionized water (1337.9 μL) and the diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Molybdenum: Molybdenum trioxide as obtained from Aldrich was mixed with a 1 M solution of oxalic acid in deionized water and the resultant mixture was heated to 60° C. until homogeneous. The resultant molybdenum oxalate solution (5.50 wt % molybdenum, 171.5 μL) was mixed with deionized water (1268.5 μL) and the diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Tungsten: Ammonium metatungstate solution was prepared by dissolving solid ammonium metatungstate hydrate as obtained from Aldrich in deionized water to 10.91 wt % metal. The prepared ammonium metatungstate solution (84.9 μL) was mixed with deionized water (1355.1 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Manganese: Manganese nitrate solution was prepared by dissolving solid manganese (II) nitrate hydrate as obtained from Aldrich to 9.46 wt % metal using deionized water. The prepared manganese nitrate solution (87.3 μL) was mixed with deionized water (1352.7 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Rhenium: A perrhenic acid solution was prepared by diluting the perrhenic acid solution as received from Aldrich to 4.986 wt % metal using deionized water. The prepared perrhenic acid solution (201.6 μL) was mixed with deionized water (1238.4 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Iron: Ferric nitrate solution was prepared by dissolving solid iron (III) nitrate hydrate as obtained from Aldrich to 3.42 wt % metal using deionized water. The prepared iron nitrate solution (275.7 μL) was mixed with deionized water (1164.3 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Ruthenium: Ruthenium nitrosyl nitrate solution was prepared by dissolving solid ruthenium nitrosyl nitrate hydrate as obtained from Alfa Aesar to 3.49 wt % metal using deionized water. The prepared ruthenium nitrosyl nitrate solution (282.7 μL) was mixed with deionized water (1157.3 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Cobalt: Cobalt nitrate solution was prepared by dissolving solid cobalt (II) nitrate hydrate as obtained from Alfa Aesar to 5.21 wt % metal using deionized water. The prepared cobalt nitrate solution (181.0 μL) was mixed with deionized water (1259.0 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Nickel: Nickel nitrate solution was prepared by dissolving solid nickel (II) nitrate hydrate as obtained from Alfa Aesar to 3.527 wt % metal using deionized water. The prepared nickel nitrate solution (272.2 μL) was mixed with deionized water (1167.8 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Copper: Copper nitrate solution was prepared by dissolving solid copper nitrate (II) hydrate as obtained from Aldrich to 3.51 wt % metal using deionized water. The prepared copper nitrate solution (278.5 μL) was mixed with deionized water (1161.5 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Gold: Hydrogen tetrachloroaurate solution was prepared by dissolving solid hydrogen tetrachloroaurate (III) hydrate as obtained from Aldrich to 3.37 wt % metal using deionized water. The prepared tetrachloroaurate solution (301.1 μL) was mixed with deionized water (1138.9 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Zinc: Zinc nitrate solution was prepared by dissolving solid zinc nitrate hydrate as obtained from Aldrich to 3.51 wt % metal using deionized water. The prepared zinc nitrate solution (276.0 μL) was mixed with deionized water (1164.0 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Gallium: Gallium nitrate solution was prepared by dissolving solid gallium (III) nitrate hydrate as obtained from Aldrich to 7.41 wt % metal using deionized water. The prepared gallium nitrate solution (116.0 μL) was mixed with deionized water (1324.0 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Iridium: Hydrogen hexachloroiridate solution was prepared by dissolving hydrogen hexachloroiridate (IV) hydrate as obtained from Aldrich to 8.08% metal using deionized water. The prepared hexachloroiridate solution (115.7 μL) was mixed with deionized water (1324.3 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Germanium: A concentrated solution of tetramethylammonium hydroxide was prepared in deionized water and solid germanium (IV) oxide as obtained from Aldrich was mixed with this solution and agitated until homogeneous. The prepared germanium oxide solution had concentrations of 9.526 wt % germanium and 15.0 wt % tetramethylammonium hydroxide. This solution (97.3 μL) was mixed with deionized water (1342.7 μL). The diluted germanium solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Tin: A concentrated solution of tetramethylammonium hydroxide was prepared in deionized water and solid tin tartrate, as obtained from Sigma and maintained at 0° C. until used, was mixed with this solution and agitated until homogeneous. The prepared tin solution had concentrations of 4.892 wt % tin and 22.7 wt % tetramethylammonium hydroxide. This solution (201.7 μL) was mixed with deionized water (1238.3 μL). The diluted tin solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Antimony: Antimony oxalate solution was prepared by mixing antimony (III) acetate as obtained from Aldrich with a 1 M solution of oxalic acid in deionized water and heating the mixture to 60° C. A concentrated solution of ammonium hydroxide in deionized water was added dropwise to the antimony containing mixture until the solution became homogeneous. At this point, the solution was diluted as-required with oxalic acid solution or deionized water to desired metal concentration. The prepared antimony oxalate solution (3.3% antimony, 290.9 μL) was mixed with deionized water (1149.1 μL) and the resultant diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Bismuth: Bismuth nitrate solution was prepared by dissolving solid bismuth (III) nitrate hydrate as obtained from Aldrich to 7.49 wt % metal in a mixture of nitric acid and deionized water such that the final concentration of nitric acid was 12.7 wt %. The prepared bismuth nitrate solution (115.7 μL) was mixed with deionized water (1324.3 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Cerium: Ammonium cerium nitrate solution was prepared by dissolving solid ammonium cerium (IV) nitrate hydrate as obtained from Aldrich to 10.03 wt % metal using deionized water. The prepared ammonium cerium nitrate solution (80.5 μL) was mixed with deionized water (1359.5 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Praseodymium: Praseodymium nitrate solution was prepared by dissolving solid praseodymium nitrate hydrate as obtained from Aldrich to 12.74 wt % metal using deionized water. The prepared praseodymium nitrate solution (64.3 μL) was mixed with deionized water (1375.7 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Neodymium: Neodymium nitrate solution was prepared by dissolving solid neodymium (III) nitrate hydrate as obtained from Aldrich to 10.9 wt % metal using deionized water. The prepared neodymium nitrate solution (78.2 μL) was mixed with deionized water (1361.8 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Samarium: Samarium nitrate solution was prepared by dissolving solid samarium (III) nitrate hydrate as obtained from Aldrich to 11.5 wt % metal using deionized water. The prepared samarium nitrate solution (73.5 μL) was mixed with deionized water (1366.5 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Europium: Europium nitrate solution was prepared by dissolving solid europium (III) nitrate hydrate as obtained from Aldrich to 14.73 wt % metal using deionized water. The prepared europium nitrate solution (53.2 μL) was mixed with deionized water (1386.8 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Gadolinium: Gadolinium nitrate solution was prepared by dissolving solid gadolinium (III) nitrate hydrate as obtained from Aldrich to 11.26 wt % metal using deionized water. The prepared gadolinium nitrate solution (75.1 μL) was mixed with deionized water (1364.9 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Terbium: Terbium nitrate solution was prepared by dissolving solid terbium (III) nitrate hydrate as obtained from Aldrich to 12.55 wt % metal using deionized water. The prepared terbium nitrate solution (65.8 μL) was mixed with deionized water (1374.2 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Dysprosium: Dysprosium nitrate solution was prepared by dissolving solid dysprosium (III) nitrate hydrate as obtained from Aldrich to 11.58 wt % metal using deionized water. The prepared dysprosium nitrate solution (73.0 μL) was mixed with deionized water (1367.0 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Holmium: Holmium nitrate solution was prepared by dissolving solid holmium (III) nitrate hydrate to 10.59 wt % metal using deionized water. The prepared holmium nitrate solution (81.8 μL) was mixed with deionized water (1358.2 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Erbium: Erbium nitrate solution was prepared by dissolving solid erbium (III) nitrate hydrate as obtained from Aldrich to 10.87 wt % metal using deionized water. The prepared erbium nitrate solution (78.4 μL) was mixed with deionized water (1361.6 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Ytterbium: Ytterbium nitrate solution was prepared by dissolving solid ytterbium (III) nitrate hydrate as obtained from Aldrich to 11.31 wt % metal using deionized water. The prepared ytterbium nitrate solution (76.0 μL) was mixed with deionized water (1364.0 μL). This diluted solution (120 μL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Magnesium: Magnesium acetate solution was prepared by dissolving solid magnesium acetate hydrate as obtained from Aldrich to 5.83 wt % metal using deionized water. The prepared magnesium acetate solution (151.1 µL) was mixed with deionized water (1288.9 µL). This diluted solution (120 µL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Calcium: Calcium acetate solution was prepared by dissolving solid calcium acetate hydrate as obtained from Aldrich to 5.9 wt % using deionized water. The prepared calcium acetate solution (158.4 µL) was mixed with deionized water (1281.6 µL). This diluted solution (120 µL) was added to the supported rhodium-indium product of the first impregnation step and agitated by vibration for 30 minutes at room temperature. The obtained trimetallic material was dried at 120° C. for 2 hours and then calcined in air at 450° C. for 4 hours.

0.6% Strontium: Strontium formate solution was prepared by dissolving solid strontium formate as obtained from Pfaltz and Bauer to 5.73 wt % metal using deionized water. The prepared strontium formate solution (169.1 µL) was mixed with deionized water (1270.9 µL). This diluted solution (120 µL) was added to the supported rhodium-indium product of the first impregnation step and agitated by vibration for 30 minutes at room temperature. The trimetallic material was dried at 120° C. for 2 hours and then calcined in air at 450° C. for 4 hours.

This series of catalysts was used to treat the same hydrocarbon feed under the same conditions as Example 1 with the exception that the prereduction step was carried out at 350° C. for 2.5 hours in a nitrogen atmosphere containing 5% hydrogen. The results summarized in Table 3 were obtained.

TABLE 3

| Catalyst (wt %) | TOS | $C_2H_2$ conv (%) | $C_2H_4$ select (%) | Green Oil select (%) |
|---|---|---|---|---|
| 0.6% Rh, 1.2% In, 0.6% Sc | 9.9 | 63.9 | 59.9 | 6.5 |
| 0.6% Rh, 1.2% In, 0.6% Y | 9.9 | 62.2 | 61.3 | 6.3 |
| 0.6% Rh, 1.2% In, 0.6% La | 9.9 | 66.7 | 58.8 | 7.3 |
| 0.6% Rh, 1.2% In, 0.6% Ti | 9.9 | 58.3 | 62.9 | 5.8 |
| 0.6% Rh, 1.2% In, 0.6% Zr | 9.9 | 48.9 | 60.6 | 6.5 |
| 0.6% Rh, 1.2% In, 0.6% Hf | 9.9 | 62.9 | 60.8 | 7.2 |
| 0.6% Rh, 1.2% In, 0.6% V | 10.4 | 72.6 | 62.6 | 6.0 |
| 0.6% Rh, 1.2% In, 0.6% Nb | 10.4 | 57.1 | 58.2 | 6.9 |
| 0.6% Rh, 1.2% In, 0.6% Ta | 10.4 | 72.2 | 58.2 | 7.0 |
| 0.6% Rh, 1.2% In, 0.6% Mo | 10.4 | 58.8 | 65.8 | 5.8 |
| 0.6% Rh, 1.2% In, 0.6% W | 10.4 | 46.8 | 65.0 | 6.3 |
| 0.6% Rh, 1.2% In, 0.6% Mn | 10.4 | 71.0 | 60.6 | 7.2 |
| 0.6% Rh, 1.2% In, 0.6% Re | 11.0 | 80.4 | 65.9 | 5.4 |
| 0.6% Rh, 1.2% In, 0.6% Fe | 11.0 | 73.8 | 65.3 | 6.1 |
| 0.6% Rh, 1.2% In, 0.6% Ru | 11.0 | 83.8 | 64.1 | 6.7 |
| 0.6% Rh, 1.2% In, 0.6% Co | 11.0 | 69.9 | 65.1 | 5.6 |
| 0.6% Rh, 1.2% In, 0.6% Ni | 11.5 | 75.5 | 62.0 | 6.0 |
| 0.6% Rh, 1.2% In, 0.6% Cu | 11.5 | 30.2 | 55.0 | 9.2 |
| 0.6% Rh, 1.2% In, 0.6% Au | 11.5 | 30.7 | 12.5 | 12.0 |
| 0.6% Rh, 1.2% In, 0.6% Zn | 11.5 | 67.5 | 66.1 | 5.2 |
| 0.6% Rh, 1.2% In, 0.6% Ga | 11.5 | 52.7 | 64.8 | 6.2 |
| 0.6% Rh, 1.2% In, 0.6% Ir | 11.5 | 26.7 | 46.2 | 18.3 |
| 0.6% Rh, 1.2% In, 0.6% Ge | 12.0 | 70.8 | 64.4 | 5.9 |
| 0.6% Rh, 1.2% In, 0.6% Sn | 12.0 | 59.8 | 59.2 | 6.8 |
| 0.6% Rh, 1.2% In, 0.6% Sb | 12.0 | 45.5 | 49.4 | 8.4 |
| 0.6% Rh, 1.2% In, 0.6% Bi | 12.0 | 27.8 | 62.0 | 6.2 |
| 0.6% Rh, 1.2% In, 0.6% Ce | 12.0 | 59.8 | 57.6 | 7.4 |
| 0.6% Rh, 1.2% In, 0.6% Pr | 12.0 | 66.5 | 58.9 | 7.8 |
| 0.6% Rh, 1.2% In, 0.6% Nd | 12.5 | 72.3 | 61.5 | 6.2 |
| 0.6% Rh, 1.2% In, 0.6% Sm | 12.5 | 66.1 | 59.2 | 5.6 |
| 0.6% Rh, 1.2% In, 0.6% Eu | 12.5 | 75.9 | 61.2 | 6.8 |
| 0.6% Rh, 1.2% In, 0.6% Gd | 12.5 | 58.7 | 60.9 | 5.6 |
| 0.6% Rh, 1.2% In, 0.6% Tb | 12.5 | 60.4 | 63.4 | 5.7 |

TABLE 3-continued

| Catalyst (wt %) | TOS | $C_2H_2$ conv (%) | $C_2H_4$ select (%) | Green Oil select (%) |
|---|---|---|---|---|
| 0.6% Rh, 1.2% In, 0.6% Dy | 12.5 | 73.7 | 60.9 | 6.6 |
| 0.6% Rh, 1.2% In, 0.6% Ho | 13.0 | 73.8 | 62.9 | 6.0 |
| 0.6% Rh, 1.2% In, 0.6% Er | 13.0 | 62.7 | 61.2 | 5.9 |
| 0.6% Rh, 1.2% In, 0.6% Yb | 13.0 | 76.3 | 59.2 | 6.9 |
| 0.6% Rh, 1.2% In, 0.6% Mg | 13.0 | 59.3 | 63.5 | 5.5 |
| 0.6% Rh, 1.2% In, 0.6% Ca | 13.0 | 49.3 | 66.5 | 6.0 |
| 0.6% Rh, 1.2% In, 0.6% Sr | 13.0 | 72.6 | 62.8 | 6.2 |

It will be seen that a majority of the trimetallic catalysts of Example 3 had a higher ethylene selectivity, and all had a lower green oil selectivity, than the catalyst of Example 1.

EXAMPLE 4

Rh—In—Ru Trimetallic Catalyst

A series of trimetallic catalysts containing rhodium, indium and ruthenium supported on alumina were produced in the same way as in Example 3 but with the relative amounts of the metals being varied and the prereduction step being conducted at 450° C. for 5 hours in a nitrogen atmosphere containing 5 mol % hydrogen.

When the catalysts were used to treat the same hydrocarbon feed under the same conditions as Example 1, the results summarized in Table 4 were obtained.

TABLE 4

| Catalyst (wt %) | TOS | $C_2H_2$ conv (%) | $C_2H_4$ select (%) | Green Oil select (%) |
|---|---|---|---|---|
| 0.6% Rh, 0.6% In, 0.3% Ru | 10.6 | 90.6 | 66.6 | 5.3 |
| 0.6% Rh, 1.2% In, 0.3% Ru | 10.6 | 79.8 | 72.7 | 4.9 |
| 0.6% Rh, 0.6% In, 1% Ru | 11.1 | 93.8 | 68.0 | 5.1 |
| 0.6% Rh, 1.2% In, 1% Ru | 11.1 | 81.5 | 73.7 | 5.2 |
| 0.6% Rh, 1.8% In, 1% Ru | 11.1 | 65.1 | 65.8 | 8.5 |
| 0.6% Rh, 0.6% In, 1.7% Ru | 11.6 | 92.5 | 67.5 | 5.4 |
| 0.6% Rh, 1.2% In, 1.7% Ru | 11.6 | 76.8 | 73.2 | 5.2 |
| 0.6% Rh, 1.8% In, 1.7% Ru | 11.6 | 63.7 | 67.7 | 6.4 |
| 0.6% Rh, 0.6% In, 2.4% Ru | 12.2 | 92.1 | 67.5 | 5.4 |
| 0.6% Rh, 1.2% In, 2.4% Ru | 12.2 | 80.8 | 72.3 | 5.3 |
| 0.6% Rh, 1.8% In, 2.4% Ru | 12.2 | 62.8 | 67.0 | 6.2 |

It will be seen from Table 4 that the use of a trimetallic Rh—In—Ru catalyst allows a high ethylene selectivity (65-74%) and a low green oil selectivity (5-8%) to be achieved at a high acetylene conversion (90% or more).

EXAMPLE 5

Rh—In—Fe Trimetallic Catalyst

A series of trimetallic catalysts containing 0.6 wt % rhodium, 1.2 wt % indium and varying amounts of iron supported on alumina were produced in the same way as in Example 3 but with the order of addition of the metals to the alumina support being varied as follows:

(a) co-impregnation of Rh/In/Fe with the alumina;

(b) impregnation of Fe followed by co-impregnation of Rh/In; and (c) co-impregnation of Rh/In followed by impregnation of Fe.

Again, the prereduction step was conducted at 450° C. for 5 hours in a nitrogen atmosphere containing 5 mol % hydrogen.

When the catalysts were used to treat the same hydrocarbon feed under the same conditions as Example 1, the results summarized in Table 5 were obtained.

TABLE 5

| Fe (wt %) | Metal Addition | TOS | $C_2H_2$ conv (%) | $C_2H_4$ select (%) | Green Oil select (%) |
|---|---|---|---|---|---|
| 0.6 | (c) | 10.1 | 99.4 | 74.3 | 5.9 |
| 0.6 | (a) | 10.1 | 90.0 | 70.7 | 8.4 |
| 2.2 | (c) | 10.7 | 97.1 | 72.2 | 5.7 |
| 2.2 | (b) | 10.7 | 99.4 | 74.8 | 5.9 |
| 1.75 | (a) | 10.7 | 98.7 | 71.5 | 7.9 |
| 3.7 | (c) | 11.2 | 99.9 | 73.0 | 6.4 |
| 3.7 | (b) | 11.2 | 99.8 | 73.9 | 6.2 |
| 2.9 | (a) | 11.2 | 99.6 | 71.4 | 8.0 |
| 5.3 | (c) | 11.8 | 99.9 | 72.9 | 6.4 |
| 5.3 | (b) | 11.8 | 99.9 | 73.5 | 6.3 |
| 4.1 | (a) | 11.8 | 99.8 | 70.5 | 8.3 |
| 6.9 | (c) | 12.3 | 99.9 | 72.8 | 6.3 |
| 6.9 | (b) | 12.3 | 99.9 | 73.7 | 6.2 |
| 5.2 | (a) | 12.3 | 99.8 | 71.1 | 7.9 |
| 8.4 | (c) | 12.9 | 99.9 | 71.8 | 6.7 |
| 8.4 | (b) | 12.9 | 99.9 | 73.8 | 6.2 |
| 6.4 | (a) | 12.9 | 99.6 | 70.6 | 8.0 |
| 10 | (c) | 13.4 | 95.7 | 73.3 | 6.4 |
| 10 | (b) | 13.4 | 99.9 | 73.5 | 6.2 |
| 7.5 | (a) | 13.4 | 99.8 | 70.0 | 8.4 |

It will be seen from Table 5 that the use of a trimetallic Rh—In—Fe catalyst allows a high ethylene selectivity (>70%) and a low green oil selectivity (6-9%) to be achieved at a high acetylene conversion (90-100%).

EXAMPLE 6

Rh—In—Fe Trimetallic Catalysts with Low RH Loading

A series of trimetallic catalysts containing 0.2 wt % rhodium, 7 wt % iron and varying amounts of indium supported on alumina were produced in the same way as in Example 3, with the iron being impregnated first, and followed by a simultaneous impregnation of rhodium and indium. Again, the prereduction step was conducted at 450° C. for 5 hours in a nitrogen atmosphere containing 5 mol % hydrogen.

When the catalysts were used to treat the same hydrocarbon feed under the same conditions as Example 1, the results summarized in Table 6 were obtained.

TABLE 6

| Catalyst (wt %) | TOS | $C_2H_2$ conv (%) | $C_2H_4$ select (%) | Green Oil select (%) |
|---|---|---|---|---|
| 0.2% Rh, 0.4% In, 7% Fe | 16.0 | 100.0 | 73.8 | 7.2 |
| 0.2% Rh, 0.5% In, 7% Fe | 16.5 | 99.3 | 73.6 | 6.5 |
| 0.2% Rh, 0.3% In, 7% Fe | 15.5 | 99.2 | 72.5 | 7.4 |
| 0.2% Rh, 0.6% In, 7% Fe | 17.1 | 99.1 | 71.8 | 6.5 |
| 0.2% Rh, 0.2% In, 7% Fe | 14.9 | 97.8 | 70.5 | 8.0 |

It will be seen from Table 6 that with the Rh—In—Fe catalyst system, very high acetylene conversion activity and good selectivities can be achieved even at low rhodium loadings.

EXAMPLE 7

Rh—In—Co Trimetallic Catalyst

A series of catalysts containing 0.3 wt % rhodium and varying amounts of indium and cobalt supported on alumina were produced by incipient wetness impregnation of the alumina with a cobalt nitrate solution and then with a solution containing rhodium and indium nitrates. After each impregnation step the catalyst precursor was calcined for 4 hours in air according to one of the following regimes:

(a) calcine at 550° C. after Co addition and at 550° C. after Rh/In addition;
(b) calcine at 550° C. after Co addition and at 450° C. after Rh/In addition;
(c) calcine at 450° C. after Co addition and at 550° C. after Rh/In addition;
(d) calcine at 450° C. after Co addition and at 450° C. after Rh/In addition;

Again, a prereduction step was conducted at 450° C. for 5 hours in a nitrogen atmosphere containing 5 mol % hydrogen.

When the catalysts were used to treat the same hydrocarbon feed under the same conditions as Example 1, the results summarized in Table 7 were obtained.

TABLE 7

| Catalyst (wt %) | Calc. | TOS | $C_2H_2$ conv (%) | $C_2H_4$ select (%) | Green Oil select (%) |
|---|---|---|---|---|---|
| 0.3% Rh, 1.2% In, 9% Co | (a) | 12.7 | 97.5 | 70.8 | 7.5 |
| 0.6% Rh, 1.6% In, 5% Co | (b) | 13.2 | 96.2 | 68.5 | 6.6 |
| 0.3% Rh, 1.2% In, 9% Co | (b) | 11.1 | 95.2 | 69.4 | 6.9 |
| 0.3% Rh, 0.8% In, 9% Co | (c) | 12.7 | 94.4 | 67.4 | 8.4 |
| 0.3% Rh, 1.2% In, 4.9% Co | (a) | 12.2 | 94.2 | 70.5 | 6.6 |
| 0.3% Rh, 0.8% In, 9% Co | (d) | 11.1 | 94.2 | 67.7 | 7.7 |
| 0.3% Rh, 1.2% In, 9% Co | (d) | 11.1 | 93.8 | 66.7 | 8.2 |
| 0.3% Rh, 0.8% In, 4.9% Co | (c) | 12.2 | 92.8 | 68.1 | 6.6 |
| 0.3% Rh, 1.2% In, 9% Co | (c) | 12.7 | 92.6 | 65.7 | 9.2 |

It will be seen from Table 7 that a high acetylene conversion activity together with good selectivities to ethylene and green oil can also be achieved with a trimetallic Rh—In—Co catalyst.

EXAMPLE 8

Pt—In—Ni Catalyst

A catalyst containing platinum, indium and nickel was prepared in the following manner.

A solution of tetraammineplatinum nitrate was prepared by dissolving solid tetraammineplatinum nitrate as obtained from Aldrich to 3.5 wt % platinum using deionized water. A solution of indium nitrate was prepared by dissolving solid indium nitrate as obtained from Prochem to 11.05 wt % indium using deionized water. A solution of nickel nitrate was prepared by dissolving solid nickel nitrate as obtained from Alfa Aesar to 13.24 wt % nickel using deionized water. An impregnation solution was then prepared by mixing the prepared platinum solution (73.9 µL), the prepared indium solution (311.5 µL) and the prepared nickel solution (226.6 µL) with deionized water (108.0 µL). This impregnation solution (120 μL) was then added to 148 mg of Norton SA6175 alumina, which had been heat treated at 975° C. for 15 minutes to convert gamma phase to theta phase, and agitated by vibration for 30 minutes at room temperature. The obtained trimetallic material was dried at 120° C. for 2 hours and then calcined in air at 450° C. for 4 hours.

The catalyst was used to treat the same hydrocarbon feed under the same conditions as Example 1 with the exception that the prereduction step was carried out at 350 C. for 2.5 hours in a nitrogen atmosphere containing 5% hydrogen. The results summarized in Table 8 were obtained.

TABLE 8

| Ex. | Catalyst (% by wt) | $C_2H_2$ conv (%) | $C_2H_4$ select (%) | Green Oil select (%) |
|---|---|---|---|---|
| 29 | 0.3% Pt, 5.0% In, 5.0% Ni | 99 | 48 | 20 |

It will be seen that the Pt—In—Ni catalyst of Example 8 was inferior to the Rh-based catalysts but nevertheless had significantly higher acetylene conversion and produced slightly less green oil than the catalyst of Example 1.

While the present invention has been described and illustrated by reference to particular embodiments, those of ordinary skill in the art will appreciate that the invention lends itself to variations not necessarily illustrated herein. For example, it is within the scope of this invention to produce a catalyst composition comprising four or more different metal components. For this reason, reference should be made solely to the appended claims for purposes of determining the true scope of the present invention.

The invention claimed is:

1. A process for selectively removing alkynes or diolefins from a feedstock also containing olefins, the process comprising contacting the feedstock with hydrogen in the presence of a catalyst composition made by the method comprising:
   (a) applying a rhodium compound to a support;
   (b) applying an indium compound to the support; and
   (c) applying a further metal compound selected from the group consisting of at least one of iron, cobalt, and ruthenium compounds to the support; and
   (d) hydrogenating the alkynes or diolefins in the feedstock with high selectivity to olefins and low selectivity to oligomers and saturates.

2. The process of claim 1 further comprising recovering an olefin-enriched product stream containing less than 10 weight % oligomerized alkyne and diolefin compounds, based on the weight of said oligomerized alkyne and diolefin compounds in said product stream by the weight of said feedstock.

3. The process of claim 1 wherein the rhodium compound and the indium compound are applied to the support concurrently.

4. The process of claim 1 wherein the indium compound is applied to the support before the rhodium compound.

5. The process of claim 1 wherein the rhodium compound is rhodium nitrate.

6. The process of claim 1 wherein the indium compound is indium nitrate or indium formate.

7. The process of claim 1 wherein at least one of the compounds is applied to the support by impregnating the support with a solution of the compound.

8. The process of claim 1 wherein at least one of the compounds is applied to the support by precipitating the compound from a solution containing ions of the associated metal.

9. A process for selectively removing alkynes or diolefins from a feedstock also containing olefins, the process comprising contacting the feedstock with hydrogen in the presence of a catalyst composition comprising:
   (a) a first component comprising rhodium;
   (b) a second component comprising indium; and
   (c) a further metal component selected from the group consisting of at least one of iron, cobalt, and ruthenium; and
   (d) hydrogenating the alkynes or diolefins in the feedstock with high selectivity to olefins and low selectivity to oligomers and saturates.

10. The process of claim 9 wherein the alkynes or diolefins have 2 to 4 carbon atoms and the feedstock also contains C2 to C4 olefins.

11. The process of claim 9 wherein said contacting is conducted at a temperature of from about 20° C. to about 150° C., a pressure of from about 690 kPa to 4100 kPa, and a molar ratio of hydrogen to alkynes and diolefins of from about 1 to about 1000.

12. The process of claim 9 wherein said contacting is conducted at a temperature of from about 30° C. to about 100° C., a pressure of from about 1400 kPa to 3400 kPa, and a molar ratio of hydrogen to alkynes and diolefins of from about 1.1 to about 800.

13. The process of claim 9 wherein said further metal compound is applied to the support before either the rhodium compound or the indium compound.

14. The process of claim 9 wherein said catalyst composition further comprises another metal component.

15. The process of claim 14 wherein said another metal component is an element of claims 2 to 15 of the Periodic Table.

16. The process of claim 15 wherein said another metal component is selected from scandium, yttrium, lanthanum, titanium, zirconium, hafnium, vanadium, niobium, tantalum, molybdenum, tungsten, manganese, rhenium, nickel, copper, gold, zinc, gallium, iridium, germanium, tin, antimony, bismuth, cesium, praseodymium, neodymium, samarium, europium, gadolinium, terbium, dysprosium, holmium, erbium, ytterbium, magnesium, calcium, and strontium.

17. The process of claim 9 with an alkyne or diolefin conversion in excess of 80%, an olefin selectivity in excess of 50%, and an oligomer selectivity of less than 20%.

18. The process of claim 17 with an alkyne or diolefin conversion in excess of 60%, an olefin selectivity in excess of 60%, and an oligomer selectivity of less than 10%.

* * * * *